United States Patent
Truong

(10) Patent No.: US 11,389,584 B2
(45) Date of Patent: Jul. 19, 2022

(54) PRIMING SYSTEM FOR INFUSION DEVICES

(71) Applicant: Avent, Inc., Alpharetta, GA (US)

(72) Inventor: Hector Dung Truong, Westminster, CA (US)

(73) Assignee: Avent, Inc., Alpharetta, GA (US)

( * ) Notice: Subject to any disclaimer, the term of this patent is extended or adjusted under 35 U.S.C. 154(b) by 249 days.

(21) Appl. No.: 16/627,828

(22) PCT Filed: Jul. 6, 2017

(86) PCT No.: PCT/US2017/040806
§ 371 (c)(1),
(2) Date: Dec. 31, 2019

(87) PCT Pub. No.: WO2019/009898
PCT Pub. Date: Jan. 10, 2019

(65) Prior Publication Data
US 2021/0146039 A1 May 20, 2021

(51) Int. Cl.
*A61M 5/145* (2006.01)
*A61M 5/168* (2006.01)
(Continued)

(52) U.S. Cl.
CPC ...... *A61M 5/1452* (2013.01); *A61M 5/16804* (2013.01); *A61M 5/145* (2013.01);
(Continued)

(58) Field of Classification Search
CPC ...... A61M 2005/1402; A61M 5/14526; A61M 5/16804; A61M 5/1452; A61M 5/1407;
(Continued)

(56) References Cited

U.S. PATENT DOCUMENTS 3,935,111 A    1/1976 Bentley
4,005,710 A    2/1977 Zeddies et al.
(Continued)

FOREIGN PATENT DOCUMENTS

EP    3372262 A    9/2018
WO    WO 93/25269 A1    12/1993
(Continued)

OTHER PUBLICATIONS

International Search Report and Written Opinion for PCT/US2017/040806, dated Mar. 6, 2018, 13 pages.

*Primary Examiner* — Nilay J Shah
(74) *Attorney, Agent, or Firm* — Meunier Carlin & Curfman LLC

(57) ABSTRACT

Priming systems and infusion assemblies are provided. For example, a priming system comprises a priming conduit having a priming portion and a pressure portion. The priming portion is in fluid communication with a first fluid source, with an inlet and an outlet for ingress and egress of a first fluid from the first fluid source. The pressure portion is in fluid communication with a second fluid source connected by a connector. Disposed within the priming conduit are a biasing member and a valve having an open position and a closed position. The biasing member is in operable communication with the valve to urge the valve into the closed position such that the valve defaults to the closed position. The open position allows the first fluid to flow from the inlet to the outlet and the closed position prevents the first fluid from flowing from the inlet to the outlet.

18 Claims, 3 Drawing Sheets

(51) Int. Cl.
  *A61M 5/14* (2006.01)
  *F04D 9/04* (2006.01)
  *A61M 39/22* (2006.01)
  *F04D 9/00* (2006.01)

(52) U.S. Cl.
  CPC ... *A61M 5/1407* (2013.01); *A61M 2005/1402* (2013.01); *A61M 2039/224* (2013.01); *A61M 2205/0216* (2013.01); *A61M 2205/3337* (2013.01); *F04D 9/004* (2013.01); *F04D 9/006* (2013.01); *F04D 9/043* (2013.01)

(58) Field of Classification Search
  CPC .... A61M 2205/3337; A61M 2039/224; A61M 2039/226; A61M 5/145; F04D 9/00; F04D 9/004; F04D 9/006; F04D 9/008; F04D 9/043; F04D 9/049
  See application file for complete search history.

(56) References Cited

U.S. PATENT DOCUMENTS

| | | |
|---|---|---|
| 4,437,859 A | 3/1984 | Whitehouse et al. |
| 5,011,477 A | 4/1991 | Winchell et al. |
| 5,127,904 A | 7/1992 | Loo et al. |
| 5,248,300 A | 9/1993 | Bryant et al. |
| 5,334,315 A | 8/1994 | Matkovich et al. |
| 5,356,379 A * | 10/1994 | Vaillancourt ........ A61M 5/1424 604/131 |
| 5,743,894 A | 4/1998 | Swisher |
| 6,306,074 B1 | 10/2001 | Waksman et al. |
| 6,550,493 B2 * | 4/2003 | Williamson ......... A47G 21/185 137/494 |
| 6,650,929 B1 | 11/2003 | Nemoto et al. |
| 8,372,045 B2 | 2/2013 | Needle et al. |
| 9,132,233 B2 | 9/2015 | Lee |
| 2002/0189684 A1 | 12/2002 | Williamson et al. |
| 2006/0122562 A1 | 6/2006 | Needle et al. |
| 2007/0293821 A1* | 12/2007 | Yribarren ............. A61M 25/10 604/131 |
| 2010/0274179 A1 | 10/2010 | Derichs |
| 2015/0083133 A1* | 3/2015 | Dunn ................... A61M 39/223 128/204.21 |

FOREIGN PATENT DOCUMENTS

| | | |
|---|---|---|
| WO | WO 01/10485 A1 | 2/2001 |
| WO | WO 01/91829 A2 | 12/2001 |
| WO | WO 02/101269 A2 | 12/2002 |
| WO | WO 2017/003937 A1 | 1/2017 |

* cited by examiner

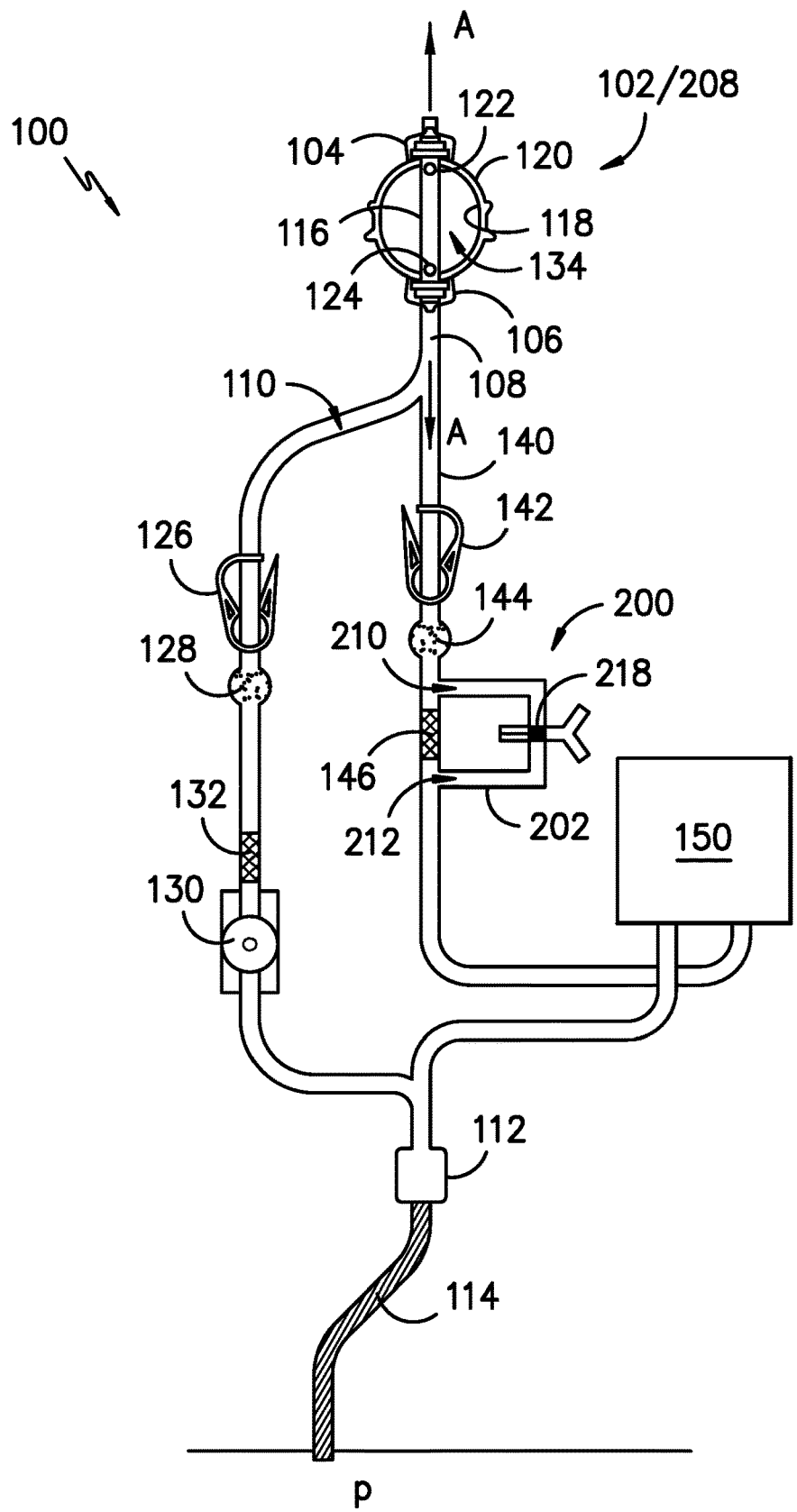
FIG. -1-

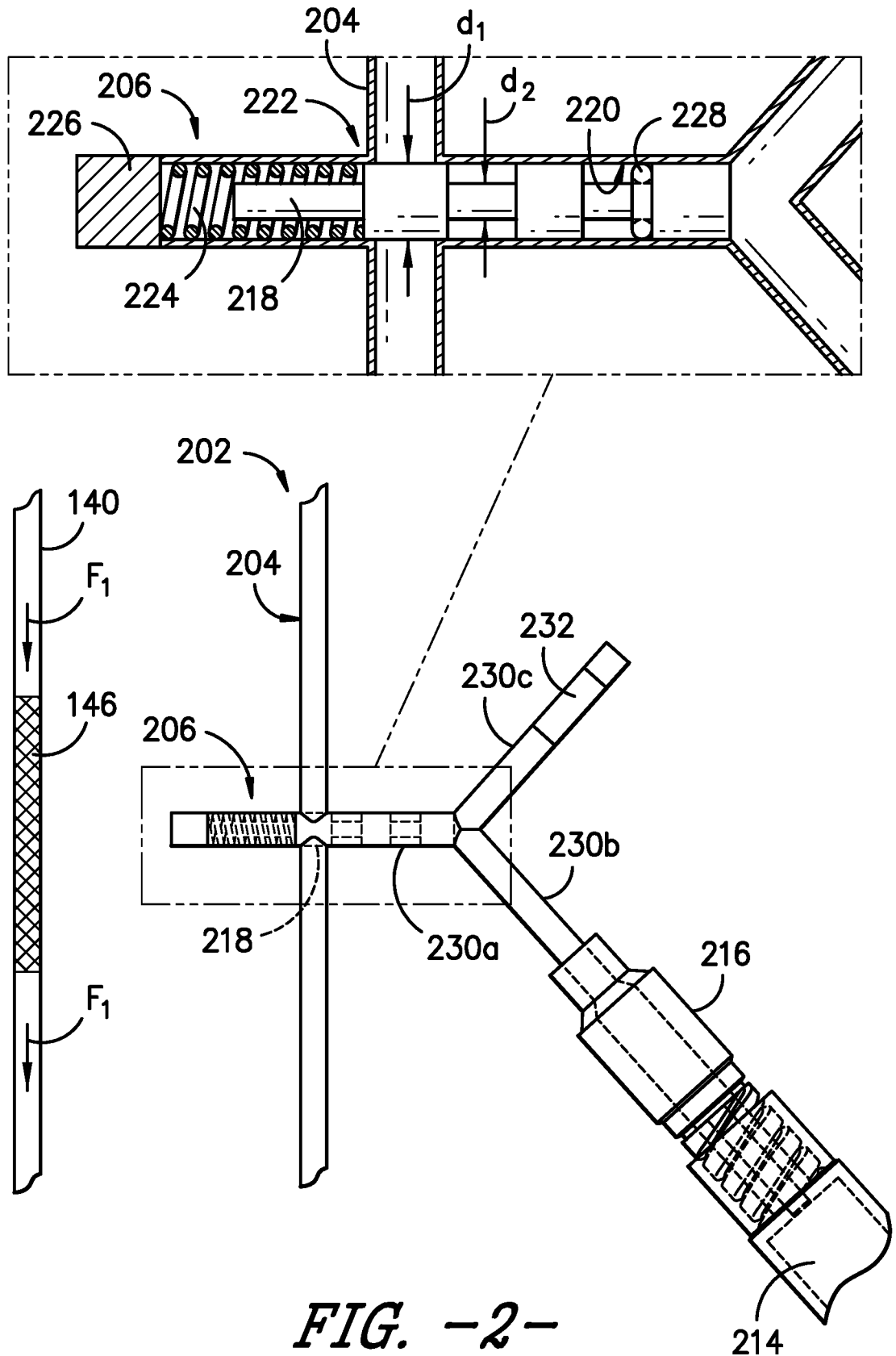
FIG. -2-

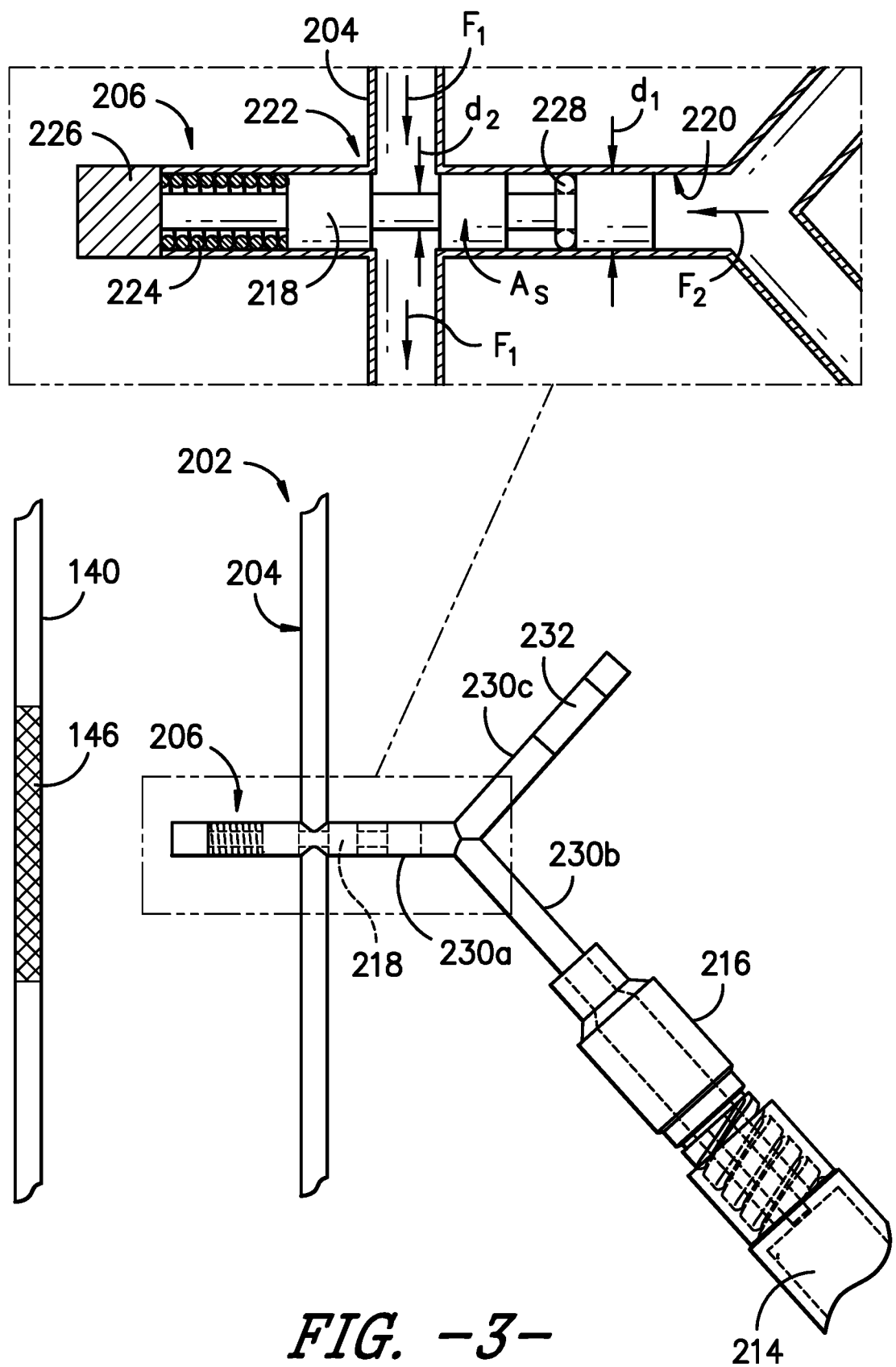
FIG. -3-

PRIMING SYSTEM FOR INFUSION DEVICES

CROSS-REFERENCE TO RELATED APPLICATIONS

This application is a national phase of and claims priority to PCT/US2017/040806, filed Jul. 6, 2017, the contents of which are incorporated herein by reference thereto.

FIELD

The present invention relates to fluid dispensing apparatus and pertains particularly to features for priming components of infusion assemblies.

BACKGROUND

In instances of severe pain, infection, and other medical ailments, it has been proven beneficial to administer a continuous flow of medicinal fluid to a patient through a catheter-based system. There are many types of medicinal fluids that can be administered in this manner including, but not limited to, insulin, analgesics, and antibiotics. Often, patients are intravenously supplied with the medicinal fluid, e.g., a pharmaceutically active liquid, at a controlled rate over a long period of time. The medicinal fluid also may be delivered to a patient's intramuscular space. Preferably, such infusion is accomplished while the patient is in an ambulatory state. Typically, an infusion assembly includes an inflatable elastomeric pump forming a liquid container that is supported by a mandrel, as well as a flow control valve or device and tubing for supply of the liquid to the patient. The walls of the pump are forced to expand when filled with the liquid and provide pressure for expelling the liquid.

Some infusion assemblies include components such as a flow rate selector and/or a device for providing a bolus of the medicinal fluid. Such components must be primed before use, e.g., to remove air from a reservoir in and/or the flow path through such components. Typically, a bolus device includes a prime key, which lifts up a clamp that acts as a flow restrictor on tubing to fill the device such that the prime key prevents flow restriction to the bolus device during priming of the device. However, such prime keys are prone to breakage and/or misuse that could allow a complete bypass of the bolus fill restrictor, which could result in an overdose of medication to the patient, e.g., by failing to limit the bolus dosage over a period of time and/or by allowing a larger bolus dose than is medically indicated. On the other hand, without bypassing such flow restrictors during priming, priming may be a slow, cumbersome process.

Accordingly, priming systems that include one or more safety mechanisms for preventing over-administration of medication, as well as one or more features for facilitating faster or rapid priming of devices would be desirable. Infusion assemblies incorporating such priming systems also would be advantageous.

SUMMARY

Aspects and advantages of the invention will be set forth in part in the following description, or may be obvious from the description, or may be learned through practice of the invention.

In one aspect, the present subject matter is directed to a priming system. The priming system comprises a priming conduit having a priming portion and a pressure portion. The priming portion is in fluid communication with a first fluid source and has an inlet for ingress of a first fluid from the first fluid source and an outlet for egress of the first fluid. The pressure portion includes a connector for connecting a second fluid source such that the pressure portion is in fluid communication with the second fluid source. The priming system further comprises a valve disposed within the priming conduit. The valve has an open position and a closed position. The priming system also comprises a biasing member disposed within the priming conduit. The biasing member is in operable communication with the valve to urge the valve into the closed position such that the valve defaults to the closed position. The valve is disposed between the inlet and the outlet of the priming portion such that the open position of the valve is configured to allow the first fluid to flow from the inlet to the outlet and the closed position of the valve is configured to prevent the first fluid from flowing from the inlet to the outlet. It will be understood that the priming system may be further configured with any additional or alternative features described herein.

In some embodiments, the priming conduit further comprises a stop, and the biasing member is in contact with the stop such that the biasing member works against the stop to control the position of the valve. Moreover, the pressure portion of the priming conduit may comprise a plug, e.g., to help build, generate, or create pressure within the pressure portion. Further, the connector may be a luer connector, and the second fluid source may be a syringe that supplies a positive pressure to the pressure portion. In other embodiments, the second fluid source is a vacuum source that creates a negative pressure within the pressure portion. The first fluid source may be an infusion pump.

In still other embodiments, the priming system includes a seal disposed between the valve and the pressure portion of the priming conduit to prevent the second fluid from flowing into the priming portion. The valve may be a piston and the seal an O-ring that extends about the piston in contact with an inner surface of the pressure portion of the priming conduit. In some embodiments where the valve is a piston, the piston valve has a surface area, as well as a varying diameter to minimize the surface area in contact with the priming conduit.

In another aspect, the present subject matter is directed to an infusion assembly. The infusion assembly comprises an elastomeric pump configured to provide a fluid under pressure, a flow path in fluid communication with the pump for providing a continuous and substantially constant flow rate of fluid from the pump, a bolus flow path for the delivery of a bolus dose of the fluid, and a bolus delivery device positioned within the bolus flow path. The infusion assembly further comprises a priming system in fluid communication with the bolus flow path and configured to receive fluid from the pump to prime the bolus delivery device. The priming system includes a priming conduit having a priming portion and a pressure portion. The priming portion is in fluid communication with the pump and has an inlet for ingress of the fluid from the pump and an outlet for egress of the fluid. The pressure portion includes a connector for connecting a second fluid source such that the pressure portion is in fluid communication with the second fluid source. The priming system also includes a valve disposed within the priming conduit. The valve has an open position and a closed position. The priming system further includes a biasing member disposed within the priming conduit. The biasing member is in operable communication with the valve to urge the valve into the closed position such that the valve defaults to the closed position. The valve is disposed between the inlet and the outlet of the priming portion such that the open position of the valve is configured to allow the fluid to flow from the inlet to the outlet and the closed position of the valve is configured to prevent the fluid from flowing from the inlet to the outlet. It will be appreciated that the priming system may be further configured with any additional or alternative features described herein.

In some embodiments, a flow restrictor is positioned within the bolus flow path, and the priming conduit bypasses the flow restrictor such that the inlet of the priming portion is in fluid communication with the bolus flow path upstream of the flow restrictor and the outlet of the priming portion is in fluid communication with the bolus flow path downstream of the flow restrictor. Further, the second fluid source may provide a second fluid to the pressure portion to move the valve from the closed position to the open position. In some embodiments, the priming conduit also comprises a stop, and the biasing member is in contact with the stop such that the biasing member works against the stop to control the position of the valve.

In still other embodiments, the connector is a luer connector. The second fluid source may be a syringe that supplies a positive pressure to the pressure portion. In other embodiments, the second fluid source is a vacuum source that creates a negative pressure within the pressure portion.

In further embodiments, a seal is disposed between the valve and the pressure portion of the priming conduit to prevent the second fluid from flowing into the priming portion. The valve may be a piston and the seal an O-ring that extends about the piston in contact with an inner surface of the pressure portion of the priming conduit. Moreover, in embodiments in which the valve is a piston, the piston valve may have a surface area, as well as a varying diameter to minimize the surface area in contact with the priming conduit.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a schematic view of an infusion assembly having a bolus delivery device according to an exemplary embodiment of the present subject matter.

FIG. 2 is a schematic view of a priming system for priming the bolus delivery device of the infusion assembly of FIG. 1, with the priming system in its default closed state, according to an exemplary embodiment of the present subject matter.

FIG. 3 is the schematic view of the priming system of FIG. 2, with the priming system in an open state.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

Further, the detailed description uses numerical and letter designations to refer to features in the drawings. Like or similar designations in the drawings and description have been used to refer to like or similar parts of the invention. As used herein, the terms "first," "second," and "third" may be used interchangeably to distinguish one component from another and are not intended to signify location or importance of the individual components.

Referring to the drawings, FIG. 1 provides a side view of an infusion assembly, e.g., for dispensing a fluid to a patient, according to an exemplary embodiment of the present subject matter. As shown, the exemplary infusion assembly 100 includes an elastomeric pump 102 having an upper support member 104 and a lower support member 106. Infusion assembly 100 defines an axial direction A, and lower support member 106 is spaced apart from upper support member 104 along the axial direction A.

More particularly, pump 102 defines a reservoir that serves as a pressurized fluid source, holding medicinal fluid, such as local anesthetics, and providing a source of fluid under pressure. Pump 102 forces the medicinal fluid through a tubing or conduit 108. Conduit 108 forms a continuous flow path 110 for delivery of the medicinal fluid into a wound site nerve bundle or the blood stream of a patient P. In the depicted exemplary embodiment, conduit or tubing 108 defines an outlet 112 connecting the continuous flow path 110 to a catheter 114 that delivers the medicinal fluid to patient P. In such embodiments, conduit 108 and catheter 114 may together define continuous flow path 110 from pump 102 to patient P.

Further, in some embodiments, infusion assembly 100 may be configured to provide for bolus delivery. In such configurations, conduit 108 may split into a continuous or primary flow path 110 and a controlled bolus flow path 140. Thus, medicinal fluid may be delivered into a wound site nerve bundle or the blood stream of patient P from pump 102 via the continuous or primary flow path or from a bolus delivery device 150 via the controlled bolus flow path.

Pump 102 preferably accommodates a volume 134 from about 100 to 500 ml of fluid under a pressure of up to approximately 30 psi. In some embodiments, the pump may hold the fluid under a pressure of about 10 psi to about 30 psi and, in other embodiments, under a pressure of about 15 psi to about 25 psi. More particularly, pump 102 has an inner core 116 extending between upper support member 104 and lower support member 106 along axial direction A. Inner core 116 is surrounded by an elastomeric bladder 118 within a housing 120. Inner core 114 preferably has an inlet port 122, e.g., to fill bladder 118 with fluid, and an outlet port 124 in fluid communication with conduit 108, e.g., to dispense the fluid from bladder 118 to patient P through flow path 110. Fluid is held under pressure within elastomeric bladder 118 and flows from elastomeric bladder 118 into conduit 108 through outlet port 124, preferably flowing at a controlled and predictable rate. Alternatively, conduit 108 may be sized to serve as a flow restrictor. Further, elastomeric bladder 118 preferably is constructed from a resilient material that may comprise a variety of elastomeric compositions well known in the art, including vulcanized synthetic polyisoprenes, natural latex, natural rubber, synthetic rubber, silicone rubber, or the like.

Exemplary pumps are described in U.S. Pat. Nos. 7,959,623 and 5,254,481, which are hereby incorporated by reference. A variety of other conventional pumps also may be used. For example, the pumps described in U.S. Pat. Nos. 5,080,652 and 5,105,983, which are hereby incorporated by reference, may be used. As will be understood by those of skill in the art, other suitable electronic or mechanical pumps offered by other manufacturers may be used as well.

Continuing with FIG. 1, an optional clamp 126 is positioned in flow path 110 downstream from pump 102. Clamp 126 can compress conduit 108 such that fluid flow from pump 102 through flow path 110 is occluded. Such occlusion is advantageous, e.g., for the transportation and preparation of infusion assembly 100 as described herein. An exemplary clamp 126 is described in U.S. Pat. No. 6,350,253, which is hereby incorporated by reference. However, a variety of other conventional clamps known in the industry may be used to occlude the flow of fluid from pump 102 through flow path 110, such as compression clamps, C clamps, roller clamps, and the like.

An optional filter 128 downstream of clamp 126 separates the fluid from contaminates and other undesired particles that may be found within the fluid. Filter 128 also preferably eliminates air from fluid flow path 110. One such filter 128 is described in U.S. Pat. No. 6,350,253, which is hereby incorporated by reference. Of course, other suitable filters recognized in the industry may be used to capture undesired particles and/or remove air from the system.

As further shown in FIG. 1, an optional flow regulator 130 is positioned in continuous flow path 110. Flow regulator 130 sets the continuous and substantially constant flow rate of fluid from pump 102 to patient P via tubing 108. In some embodiments, the flow rate may be adjusted to a rate within a range, e.g., within a range of about 0.5 to about 14 cubic centimeters of fluid per hour. Flow regulator 130 may be manually adjustable, if desired, and provided with a dial, switch, or lever with an adjustable flow rate control display corresponding to the range of flow rates. For example, the flow rate range may be from about 1 to about 7 or from about 2 to about 14 cubic centimeters of fluid per hour such that the flow rate control display includes a lowermost value of 1 and an uppermost value of 7 or a lowermost value of 2 and an uppermost value of 14. It will be appreciated that the foregoing flow rate values are only exemplary, and in other embodiments, infusion assembly 100 may have other flow rates and the flow rate may be adjustable within another range of flow rates. Alternatively, a constant flow regulator (i.e., a regulator that is not adjustable) can be employed. For example, an optional flow regulating orifice, such as a glass orifice tube 132, may be employed in the primary or continuous flow path 110. Moreover, in embodiments having a bolus flow path, an optional second flow regulating orifice 146 may be employed in the bolus flow path.

The particular arrangement of clamp 126, filter 128, and flow regulator 130 (or glass tube 132) described herein is merely exemplary. These elements, if present, may be arranged in any order, as will be easily understood by those skilled in the art. Desirably, however, glass orifice tube 132 is located downstream of filter 128 when orifice tube 132 and filter 128 are provided in infusion assembly 100.

In the exemplary embodiment illustrated in FIG. 1, the conduit 108 splits into two flow paths, the continuous or primary flow path 110 and the bolus flow path 140. As previously described, a bolus delivery device 150 is in fluid communication with the bolus flow path 140. The bolus delivery device 150 accumulates a quantity of fluid from the bolus flow path 140 leading from the pump 102 and holds the fluid under pressure until the bolus dose is triggered by an actuator (not shown) for release into the patient P. The actuator of the bolus delivery device 150 may be operable by any user, such as the patient P, a caregiver, a physician, etc., to dispense a bolus dose of the medicinal fluid to the patient P.

Generally, the bolus delivery device 150 is configured to receive fluid, elastically expand to pressurize the fluid, store the pressurized fluid, and dispense the pressurized fluid while avoiding over-administration of a medicinal fluid to the patient. Downstream from the bolus delivery device 150, the continuous flow path 110 and the bolus flow path 140 converge into a single flow path. Further, as illustrated in FIG. 1, a clamp 142, a filter 144, and/or a flow restrictor 146, such as a flow regulating orifice, may be positioned in the bolus flow path 140 upstream of the device 150. The clamp 142 can compress the flow path 140 such that fluid flow from the pump 102 is occluded. Such occlusion is advantageous, e.g., for the transportation and preparation of the fluid delivery device. Moreover, the optional filter 144 downstream of clamp 142 separates the fluid from contaminates and other undesired particles that may be found within the fluid, as well as preferably eliminates air from the bolus flow path 140. Exemplary clamps and filters that may be used for clamp 142 and filter 144 are described in greater detail above with respect to clamp 126 and filter 128.

The flow restrictor 146 restricts the flow of fluid to the bolus delivery device 150, e.g., to help control the bolus refill rate. For example, fluid from the pump 102 refills a reservoir of the device 150 following the administration of a bolus dose to the patient P. By controlling the refill rate of the reservoir, the flow restrictor 146 may be one feature of the bolus system that helps prevent over-administration of medication to the patient, e.g., by limiting or restricting the delivery of additional medicinal fluid to the patient within a time period following the administration of a bolus dose of the medicinal fluid. As shown in FIG. 1, a priming system 200 is included in parallel with the flow path 140, providing a bypass circuit around the flow restrictor 146 for faster or rapid priming of the bolus delivery device 150. The priming system 200 is in fluid communication with the bolus flow path 140 and is configured to receive fluid from the pump 102 to prime the bolus delivery device 150.

Although described herein with respect to the bolus system of the infusion assembly 100, it should be appreciated that the priming system 200 described herein also may be used to prime infusion assembly tubing and/or other components of the infusion assembly 100, such as flow selection devices or the like. Of course, the priming system 200 may be used with other appropriate assemblies, devices, or systems as well.

Turning now to FIGS. 2 and 3, the priming system 200 will be described in greater detail. As shown in FIG. 2, the priming system 200 comprises a priming conduit 202 that has a priming portion 204 and a pressure portion 206. The priming portion 204 is in fluid communication with a first fluid source 208 that provides a first fluid $F_1$ to the priming system 200. The priming portion 204 has an inlet 210 for ingress of the first fluid $F_1$ from the first fluid source 208 and an outlet 212 for egress of the first fluid $F_1$ from the priming system 200. In the depicted embodiment, the first fluid source 208 is the pump 102, which provides medicinal fluid to the bolus flow path 140 such that the medicinal fluid is the first fluid $F_1$ in the exemplary embodiment. In other embodiments, the first fluid source 208 and first fluid $F_1$ may be any suitable fluid source and fluid provided by such fluid source. The first fluid $F_1$ flows into the bolus flow path 140 and, under certain conditions described in greater detail below, bypasses the flow restrictor 146 by flowing into the priming portion 204 of the priming system 200. The first fluid $F_1$ may then flow to the bolus delivery device 150, e.g., to prime the device 150 and its associated tubing.

The pressure portion 206 of priming system 200 is in fluid communication with a second fluid source 214 that provides a second fluid $F_2$ to the priming system 200. More particularly, the pressure portion 206 includes a connector 216 for connecting the second fluid source 214 to the pressure portion. In the depicted embodiment, the connector 216 is a luer connector and the second fluid source 214 is a syringe that supplies a second fluid $F_2$ such as saline or the like, but in other embodiments, other types of connectors 216, fluid sources 214, and second fluids $F_2$ also may be used. For example, the second fluid source 214 may be a vacuum source that generates or supplies a vacuum within the pressure portion 206. Thus, in various embodiments, the second fluid source 214 and second fluid $F_2$ may generate either a positive pressure or a negative pressure within the pressure portion 206 of the priming conduit 202.

As shown in FIGS. 2 and 3, a gate or valve 218 is disposed within the priming conduit 202. In the illustrated embodiment, the valve 218 is a piston or plunger disposed in the pressure portion 206 of the priming conduit 202, but the valve 218 may have any suitable configuration. Further, the valve 218 has a closed position, as shown in FIG. 2, and an open position, as illustrated in FIG. 3. In the depicted embodiment where valve 218 is a piston, the piston 218 has a varying diameter d; more particularly, the piston 218 has a first diameter $d_1$ and a second diameter $d_2$. The first diameter $d_1$ is in contact with an inner surface 220 of the priming portion 206, and the second diameter $d_2$ is smaller than the first diameter $d_1$. As such, the segments of the piston 218 having the second diameter $d_2$ do not contact the inner surface 220 of the priming portion 206.

As illustrated in FIGS. 1-3, the pressure portion 206 of the priming conduit 202 intersects the priming portion 204 at an intersection 222. The valve 218 spans the intersection 222 between the priming and pressure portions 204, 206 such that the closed and open positions of the valve 218 control whether the first fluid $F_1$ may flow from the inlet 210 to the outlet 212 of the priming portion 204. That is, the valve 218 is disposed between the inlet 210 and the outlet 212 of the priming portion 204 such that the open position of the valve 218 is configured to allow the first fluid $F_1$ to flow from the inlet 210 to the outlet 212, and thereby on to the bolus delivery device 150 via the bolus flow path 140, and the closed position of the valve 218 is configured to prevent the first fluid $F_1$ from flowing from the inlet 210 to the outlet 212.

More specifically, for the illustrated piston embodiment, the first diameter $d_1$ of the valve 218 spans the intersection 222 when the valve 218 is in the closed position. Because the segments of the valve 218 having the first diameter $d_1$ contact the inner surface 220 of the priming portion 206 of the priming conduit 202, the valve 218 prevents the first fluid $F_1$ from flowing across the intersection 222, i.e., the valve 218 blocks the intersection 222 and thereby prevents the first fluid $F_1$ from flowing from the inlet 210 of the priming portion 204 to the outlet 212 of the priming portion 204. However, when the valve 218 is in the open position, a segment of the valve 218 having the second diameter $d_2$ spans the intersection 222. Because the second diameter $d_2$ of the valve 218 is smaller than the first diameter $d_1$, the second diameter $d_2$ segment of the valve 218 does not block the intersection 222 of the priming and pressure portions 204, 206, and the first fluid $F_1$ may flow from the priming portion inlet 210 around the valve 218 to the priming portion outlet 212, where the first fluid $F_1$ reenters the bolus flow path 140 to flow on to the bolus delivery device 150 and any other downstream components of the infusion assembly 100.

As illustrated in FIGS. 2 and 3, the priming system 200 includes a biasing member 224, such as a spring or the like, disposed within the priming conduit 202. The biasing member 224 is in operable communication with the valve 218 to urge the valve into the closed position shown in FIG. 2. Further, the priming conduit 202 comprises a stop 226, and the biasing member 224 is in contact with the stop 226 such that the biasing member 224 works against the stop 226 to control the position of the valve 218. As shown in FIG. 2, the biasing member 224 pushes against the stop 226 to urge the valve 218 into the closed position. As depicted in FIG. 3, when the second fluid $F_2$ from the second fluid source 214 is introduced into the pressure portion 206 of the priming conduit 202, the valve 218 pushes the biasing member 224 against the stop 226 as the valve 218 moves to the open position. That is, the second fluid $F_2$ applies sufficient pressure to the valve 218 to overcome the force of the biasing member 224 and move the valve until a valve segment having the second diameter $d_2$ is positioned within the intersection 222 of the priming and pressure portions 204, 206 of the priming conduit 202. As previously described, the segment of the valve 218 having the second diameter $d_2$ does not completely block the intersection 222, such that the first fluid $F_1$ may flow past the valve 218 and through the outlet 212 of the priming portion 204. Thus, the valve 218 in the exemplary embodiment functions as a spring-loaded check valve that is opened with, e.g., water pressure supplied by the second fluid $F_2$ and second fluid source 214. However, as described above, the second fluid source 214 and second fluid $F_2$ also may utilize a negative pressure, such as a vacuum, to manipulate the position of valve 218. For instance, rather than pushing the valve 218 using a positive pressure from the second fluid source 214 and/or second fluid $F_2$, the valve 218 may be pulled using a negative pressure from the second fluid source 214 and/or second fluid $F_2$.

The piston-style valve 218 of the embodiment illustrated in FIGS. 2 and 3 has a segment having the second diameter $d_2$ between two segments that each have the first diameter $d_1$. As such, when the valve 218 is in the open position as shown in FIG. 3, the first fluid $F_1$ flows past the valve 218 but only within the priming portion 204 of the priming conduit 202. That is, the first fluid $F_1$ does not flow into the pressure portion 206 of the conduit 202. Similarly, the valve 218 and biasing member 224 are configured such that the valve 218 does not open to an extent to allow the second fluid $F_2$ to flow into the priming portion 204. In some embodiments, the priming system 200 comprises a seal 228 disposed between the valve 218 and the pressure portion 206 of the priming conduit 202 to prevent the second fluid $F_2$ from flowing into the priming portion 204, which also helps prevent the first fluid $F_1$ from flowing into the pressure portion 206. The seal 228 may be an O-ring that extends about the piston-style valve 218, as shown in the exemplary embodiment, and that is in contact with the inner surface 220 of the pressure portion 206. Of course, some embodiments may utilize more than one seal 228, such as more than one O-ring or a variety of different types of seals.

As described above, the valve 218 may have a varying diameter d; specifically, the exemplary valve 218 has a first diameter $d_1$ and a second diameter $d_2$ that is smaller than the first diameter $d_1$. The position of the first and second diameters $d_1$ and $d_2$ with respect to the intersection 222 between the priming and pressure portions 204, 206 of the priming conduit 202 determine whether the valve 218 is open, permitting the first fluid $F_1$ to flow through the priming portion 204, or closed, preventing the first fluid $F_1$ from flowing through the priming portion 204. However, the varying diameter d of the valve 218 also varies the surface area of the valve 218 in contact with the inner surface 220 of the pressure portion 206. More particularly, the valve 218, configured as a piston in the embodiment of FIGS. 2 and 3, has a surface area $A_S$. The length of each segment of the valve 218 having a diameter sufficient to contact the inner surface 220 of the pressure portion 206, i.e., the first diameter $d_1$ in the exemplary embodiment, determines the surface area $A_S$ of the valve 218 that is in contact with the inner surface 220. The varying diameter of the valve 218, e.g., the different diameters and the length of each segment of a given diameter, may be chosen to minimize the surface area $A_S$ in contact with the priming conduit 202, specifically the pressure portion 206 of the priming conduit 202. By minimizing the surface area $A_S$ in contact with the priming conduit 202, friction between the valve 218 and the priming conduit 202 may be minimized, which may help the valve 218 move between the closed and open positions.

As further illustrated in FIGS. 1-3, the pressure portion 206 of the priming conduit 202 may be generally Y shaped, with a stem 230a and two arms 230b, 230c. The stem 230a intersects the priming portion 204, and the stop 226, biasing member 224, and valve 218 are disposed within the stem 230a. The first arm 230b includes the connector 216, to which the second fluid source 214 may be attached, and the second arm 230c includes a plug 232. The plugged second arm 230c provides additional area within the pressure portion 206 to build sufficient pressure with second fluid $F_2$ to open the valve 218, i.e., when second fluid $F_2$ supplies a positive pressure within the pressure portion 206. In some embodiments, the second arm 230c and plug 232 may be omitted. For example, the pressure portion 206 of the priming conduit 202 may have a shape and/or size such that sufficient pressure is built up with the pressure portion 206 when the second fluid $F_2$ is inserted into the pressure portion 206 without the need for the second arm 230c.

With the valve 218 opened by the positive or negative pressure of the second fluid $F_2$ supplied by the second fluid source 214 as shown in FIG. 3, fluid (i.e., first fluid $F_1$) from the pump 102 (i.e., first fluid source 208) flows through the priming portion 204 of the priming conduit 202 and on through the bolus delivery device 150, which preferably includes a reservoir for receipt of a volume of fluid from the pump 102. As such, the fluid $F_1$ displaces air within the device 150, as well as any other devices downstream of the priming system 200. Once the fluid has flowed through the device 150, the second fluid source 214 may be removed, such that the valve 218 moves to the closed position illustrated in FIG. 2, and the fluid $F_1$ flows through the flow restrictor 146, rather than the priming system 200, to fill the reservoir of the device 150. At this point, the bolus delivery device 150, and any other devices downstream of the priming system 200, is primed, and the connector 216 may be removed from the priming portion 206 to prevent bypassing of the flow restrictor 146 as a second fluid source 214 cannot be positioned in fluid communication with the priming conduit 202 to supply a second fluid $F_2$ to pressurize and open the valve 218. That is, the priming system 200 permits priming of, e.g., the bolus delivery device 150 in a faster manner or reduced amount of time by bypassing the flow restrictor 146, which controls the flow rate of the medicinal fluid from pump 102 to the bolus delivery device 150. As such, the medicinal fluid reaches the bolus delivery device 150 faster when the fluid travels through the priming system 200 rather than the flow restrictor 146. If the medicinal fluid is permitted to flow through the priming system 200 to completely fill and/or refill the bolus delivery device 150, an excess or overdose of medicinal fluid could be provided to the patient P by not allowing a clinically sufficient time between bolus doses. Thus, in exemplary embodiments, the priming system 200 includes features such as a removable connector 216 to help prevent bypassing of the flow restrictor 146 outside of priming the bolus delivery device 150.

The priming system 200 also may include other safety features that, in particular, prevent bypassing the flow control provided by the flow restrictor 146 to help prevent over-administration of medication to the patient. For instance, the pressure required to move the valve 218 to the open position of FIG. 3, i.e., the cracking pressure, may be selected to ensure the valve 218 stays closed until and/or only when the second fluid source 214 applies at least the cracking pressure to the valve 218. As an example, the cracking pressure may be about 10 psi, such that the valve 218 opens when the pressure portion 206 of the priming conduit 202 is pressurized by the second fluid source 214 over 10 psi. It will be appreciated that the cracking pressure may be adjusted by, e.g., changing the spring rate where the biasing member 224 is a spring and/or changing the dimensions of the valve 218 or other components of the priming system 200. As another safety feature, the priming conduit 202, particularly the pressure portion 206, may a micro flow path to discourage and/or prevent users from sticking objects into the pressure portion 206 to try to manually open the valve 218. That is, in some embodiments of the priming system 200, at least the pressure portion 206 may have a sufficiently small diameter such that objects cannot be inserted into the pressure portion 206 to bypass the flow restrictor 146 by moving the valve 218 from the closed position of FIG. 2 to the open position of FIG. 3. The priming system 200 may incorporate other safety features as well.

Accordingly, as described herein, a system is provided for faster priming of various components of an infusion assembly. In exemplary embodiments, the priming system described herein allows faster priming of certain components of the infusion assembly by bypassing a flow restrictor that otherwise controls the flow rate of fluid to the components. However, the priming system also includes features for discouraging or preventing continuous and/or non-priming related bypassing of the flow restrictor, such that the flow rate may be controlled per the design of the infusion system. For instance, the priming system defaults to a closed position, such that the fluid of the infusion assembly is permitted to flow through the priming system, bypassing the flow restrictor, upon a positive action by a user. In particular embodiments, the positive action may be the connection of a second fluid source that applies pressure to a check valve controlling flow through the priming system, and the ability to connect the second fluid source may be disabled after priming, e.g., by removing or breaking off a connector, such that the priming system returns to its default closed position and cannot be re-opened. Other benefits and advantages of the subject matter described herein also may be realized by those of ordinary skill in the art.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A priming system, comprising:
    a priming conduit having
        a priming portion in fluid communication with a first fluid source, the priming portion having an inlet for ingress of a first fluid from the first fluid source and an outlet for egress of the first fluid, and
        a pressure portion including a connector for connecting a second fluid source such that the pressure portion is in fluid communication with the second fluid source, and a plug;
    a valve disposed within the priming conduit, the valve having an open position and a closed position; and
    a biasing member disposed within the priming conduit, the biasing member in operable communication with the valve to urge the valve into the closed position such that the valve defaults to the closed position,
    wherein the valve is disposed between the inlet and the outlet of the priming portion such that the open position of the valve is configured to allow the first fluid to flow from the inlet to the outlet and the closed position of the valve is configured to prevent the first fluid from flowing from the inlet to the outlet.

2. The priming system of claim 1, wherein the priming conduit further comprises a stop, and wherein the biasing member is in contact with the stop such that the biasing member works against the stop to control the open and closed positions of the valve.

3. The priming system of claim 1, wherein the connector is a luer connector.

4. The priming system of claim 1, wherein the first fluid source is an infusion pump.

5. The priming system of claim 1, wherein the second fluid source is a syringe supplying a positive pressure to the pressure portion.

6. The priming system of claim 1, wherein the second fluid source is a vacuum source creating a negative pressure within the pressure portion.

7. The priming system of claim 1, further comprising a seal disposed between the valve and the pressure portion of the priming conduit to prevent the second fluid from flowing into the priming portion.

8. The priming system of claim 7, wherein the valve is a piston and the seal is an O-ring extending about the piston and in contact with an inner surface of the pressure portion of the priming conduit.

9. The priming system of claim 1, wherein the valve is a piston having a surface area, and wherein the piston has a varying diameter to minimize the surface area in contact with the priming conduit.

10. An infusion assembly, comprising:
    an elastomeric pump configured to provide a fluid under pressure;
    a flow path in fluid communication with the pump for providing a continuous and substantially constant flow rate of the fluid from the pump;
    a bolus flow path for the delivery of a bolus dose of the fluid;
    a flow restrictor positioned within the bolus flow path;
    a bolus delivery device positioned within the bolus flow path; and
    a priming system in fluid communication with the bolus flow path and configured to receive the fluid from the pump to prime the bolus delivery device, the priming system including:
        a priming conduit having:
            a priming portion in fluid communication with the pump, the priming portion having an inlet for ingress of the fluid from the pump and an outlet for egress of the fluid, and
            a pressure portion including a connector for connecting a second fluid source such that the pressure portion is in fluid communication with the second fluid source;
        a valve disposed within the priming conduit, the valve having an open position and a closed position; and
        a biasing member disposed within the priming conduit, the biasing member in operable communication with the valve to urge the valve into the closed position such that the valve defaults to the closed position,
    wherein the valve is disposed between the inlet and the outlet of the priming portion such that the open position of the valve is configured to allow the fluid to flow from the inlet to the outlet and the closed position of the valve is configured to prevent the fluid from flowing from the inlet to the outlet,
    wherein the priming conduit bypasses the flow restrictor such that the inlet of the priming portion is in fluid communication with the bolus flow path upstream of the flow restrictor and the outlet of the priming portion is in fluid communication with the bolus flow path downstream of the flow restrictor.

11. The infusion assembly of claim 10, wherein the second fluid source provides a second fluid to the pressure portion to move the valve from the closed position to the open position.

12. The infusion assembly of claim 10, wherein the priming conduit further comprises a stop, and wherein the biasing member is in contact with the stop such that the biasing member works against the stop to control the open and closed positions of the valve.

13. The infusion assembly of claim 10, wherein the connector is a luer connector.

14. The infusion assembly of claim 10, wherein the second fluid source is a syringe supplying a positive pressure to the pressure portion.

15. The infusion assembly of claim 10, wherein the second fluid source is a vacuum source creating a negative pressure within the pressure portion.

16. The infusion assembly of claim 10, further comprising a seal disposed between the valve and the pressure portion of the priming conduit to prevent the second fluid from flowing into the priming portion.

17. The infusion assembly of claim 16, wherein the valve is a piston and the seal is an O-ring extending about the piston and in contact with an inner surface of the pressure portion of the priming conduit.

18. The infusion assembly of claim 10, wherein the valve is a piston having a surface area, and wherein the piston has a varying diameter to minimize the surface area in contact with the priming conduit.

\* \* \* \* \*